(12) United States Patent
Romero

(10) Patent No.: US 8,993,274 B2
(45) Date of Patent: Mar. 31, 2015

(54) ENZYMATIC HYDROLYSIS PRETREATMENT OF LIGNOCELLULOSIC MATERIALS

(75) Inventor: Rodolfo Romero, Gansevoort, NY (US)

(73) Assignee: Andritz Inc., Glens Falls, NY (US)

(*) Notice: Subject to any disclaimer, the term of this patent is extended or adjusted under 35 U.S.C. 154(b) by 0 days.

(21) Appl. No.: 13/570,848

(22) Filed: Aug. 9, 2012

(65) Prior Publication Data

US 2013/0045509 A1 Feb. 21, 2013

Related U.S. Application Data

(60) Provisional application No. 61/524,967, filed on Aug. 18, 2011, provisional application No. 61/546,462, filed on Oct. 12, 2011.

(51) Int. Cl.

| | | |
|---|---|---|
| *C12P 7/10* | (2006.01) | |
| *C12P 19/02* | (2006.01) | |
| *D21C 1/02* | (2006.01) | |
| *D21C 1/04* | (2006.01) | |
| *D21C 5/00* | (2006.01) | |
| *D21C 11/00* | (2006.01) | |

(52) U.S. Cl.
CPC .. *C12P 7/10* (2013.01); *Y02E 50/16* (2013.01); *C12P 19/02* (2013.01); *D21C 1/02* (2013.01); *D21C 1/04* (2013.01); *D21C 5/005* (2013.01); *D21C 11/0007* (2013.01)
USPC .......................................................... 435/99

(58) Field of Classification Search
None
See application file for complete search history.

(56) References Cited

PUBLICATIONS

Dowe and McMillian "SSF Experimental Protocols—Lignocellulosic Biomass Hydrolysis and Fermentation" (2001) National Renewable Energy Laboratory (NREL) 1-16.*

Wyman et al. "Comparative Sugar Recovery and Fermentation Data Following Pretreatment of Poplar Wood by Leading Technologies" (2009) Biotechnology Progress, vol. 25: 333-339.*
Zacchi et al. "Economic Evaluation of Enzymatic Hydrolysis of Phenol-Pretreated Wheat Straw" (1988) Biotechnology and Bioengineering, vol. 32: 460-466.*
Zhao et al. "Organosolv pretreatment of lignocellulosic biomass for enzymatic hydrolysis" (2009) Applied Microbiology and Technology, 82:815-827.*
Park et al. "Oganosolv pretreatment with various catalysts for enhancing enzymatic hydrolysis of pitch pine" (2010) Bioresource Technology, 101:7046-7053.*
Klinke et al. "Inhibition of ethanol-producing yeast and bacteria by degradation products produced during pre-treatment of biomass." (2004) Applied Microbiology and Biotechnology, vol. 66: 10-26.*
J. Li, et al., "Lignin depolymerization/repolymerization and its critical role for delignification of aspen wood by steam explosion", *Bioresource Technology 98*, (2007) pp. 3061-3068.
Wyman, Charles E., et. al. "Comparative Sugar Recovery and Fermentation Data Following Pretreatment of Poplar Wood by Leading Technologies," Biotechnol. Prog. Mar. 17, 2009, pp. 333-339, vol. 25, No. 2.
The State Intellectual Property Office for the People's Republic of China, "Notice of Second Office Action and Written Opinion of Examiner," Jul. 24, 2014, pp. 1 to 6.

* cited by examiner

*Primary Examiner* — Jon P Weber
*Assistant Examiner* — Teresa E Knight
(74) *Attorney, Agent, or Firm* — Nixon & Vanderhye P.C.

(57) ABSTRACT

This disclosure relates to a method for treating a biomass comprising a lignocellulosic material to produce fermentable sugars comprising the steps of treating the biomass to produce a biomass with a depolymerized lignin, adding a carbonyl scavenger to the biomass before, during, or after said treating step to inhibit repolymerization of the lignin, adding at least one of a laccase enzyme and a cellulases enzyme to the biomass with depolymerized lignin subsequently to the addition of the carbonyl scavenger, and producing a fermentable sugar from the action of the laccase enzyme and cellulases enzyme on the biomass with depolymerized lignin.

10 Claims, 3 Drawing Sheets

ENZYMATIC HYDROLYSIS PRETREATMENT OF LIGNOCELLULOSIC MATERIALS

RELATED APPLICATIONS

This application claims the benefit of priority to U.S. Provisional Applications No. 61/524,967 filed Aug. 18, 2011 and No. 61/546,462 filed Oct. 12, 2011, each of which are hereby incorporated by reference in their entirety as if fully set forth herein.

THE FIELD OF THE INVENTION

The present disclosure relates generally to the conversion of biomass such as corn stovers, wood chips and other lignocellulosic materials to commercially useful products such as hydrocarbons and fermentable sugars.

BACKGROUND

Cellulose and lignin are two of the most prominent renewable carbon sources. These two biomolecules are found together in lignocellulosic materials which include all vascular plants. Lignocellulosic materials are domestically renewable and becoming increasingly valuable a feedstock since petroleum feedstocks have become more expensive and more reliant on imported sources.

Lignin comprises roughly 25% of lignocellulosic biomass. It is formed in plants primary by polymerization of three precursors which forms cross-linked macromolecules with molecular masses in excess of 10,000. Because lignin polymerizes within itself and with the other cell wall components, it minimizes the accessibility of cellulose and hemicellulose to microbial enzymes. In its polymerized form, lignin is generally associated with reduced digestibility of the overall plant biomass, which helps defend against pathogens and pests but which hinders its commercial value.

SUMMARY OF INVENTION

A method for treating biomass has been conceived to produce fermentable sugars. The processes of the invention involve a steam pretreatment step wherein biomass is treated with a dilute acid steam treatment or steam explosion treatment to cause the depolymerization of a lignin in the biomass. Prior to, during, or following the steam pretreatment step, a carbonyl scavenger (carbonium ion scavenger) is added to prevent repolymerization of the depolymerized or to be depolymerized lignin. Then, at least one enzyme such as cellulase is added to convert cellulose and hemi-cellulose into monomeric sugar components while the carbonyl scavenger is still active in inhibiting repolymerization of the lignin. Optionally, another enzyme such as laccases may also be added to act on remaining carbonyl scavenger in the cellulose.

One embodiment of the disclosure relates to methods for treating a biomass to produce fermentable sugars. A method for treating a biomass comprising a lignocellulosic material to produce fermentable sugars comprising: treating the biomass to produce a biomass with a depolymerized lignin; adding a carbonyl scavenger to the biomass before, during or after the treating step to inhibit repolymerization of the lignin; adding at least one of a laccases enzyme and a cellulases enzyme or both enzymes to the biomass with depolymerized lignin subsequently to the addition of the carbonyl scavenger; and producing a fermentable sugar from the action of the laccases enzyme and cellulases enzyme on the biomass with depolymerized lignin. The adding of at least one of a laccases enzyme and a cellulases enzyme or both enzymes to the biomass may occur after said treating step.

The biomass may be any lignocellulosic material or may be a mixture that comprises a lignocellulosic material (e.g., a byproduct of a (industrial) process or a mixed waste product). Lignocellulosic material refers to a material that comprises (1) cellulose, hemicellulose, or a combination and (2) lignin. Throughout this disclosure, it is understood that cellulose may refer to cellulose, hemicellulose, or a combination thereof. Cellulase may refer to cellulase, hemi-cellulase, or a combination thereof.

Examples of a biomass or lignocellulosic material that can be treated with the methods of the disclosure include materials comprising corn stovers, bioenergy crops, agricultural residues, municipal solid waste, industrial solid waste, yard waste, wood and forestry waste, sugar cane, switchgrass, wheat straw, hay, barley, barley straw, rice straw, grasses, waste paper, sludge or byproducts from paper manufacture, corn grain, corn cobs, corn husks, grasses, wheat, wheat straw, hay, rice straw, sugar cane bagasse, sorghum, soy, trees, branches, wood chips, sawdust and any combination thereof.

In the first step of the process, a steam treatment, such as a dilute acid steam treatment or a steam explosion treatment is applied to the biomass. One of the goals of the steam treatment is to depolymerize the lignin in the biomass to a sufficient extent to allow an enzyme or mixture of enzymes to convert the cellulose and hemi-cellulose in the biomass into less complex sugars in a subsequent step.

Before the steam treatment, associated with (i.e., during) the steam treatment, or after the steam treatment, a carbonyl scavenger is added to the biomass to prevent repolymerization of the depolymerized lignin produced by the steam treatment. The carbonyl scavenger may be, for example, 2-naphthol or any other carbonyl scavenger. Other examples of suitable carbonyl scavengers include m-xylene, p-xylene, napththalene, phenol, o-cresol, m-cresol, p-cresol, 2,5-Xylenol, 3,5-Xylenol, 3,4-Xylenol, 2,3-Xylenol, 2,6 Xylenol, 2,4-Xylenol, Catechol, Resorcinol, Hydroquinone, 5 methyl resorcinol, 1,3-Naphthalenediol, 1-naphthol anthraquinone, 2 Ethylanthraquinone, p-hydroxybenzoic acid, or $SO_2$(Sulfur Dioxide). The scavengers may be used individually or in any combination.

Following the steam treatment and the addition of the carbonyl scavenger, at least one enzyme is added to digest the cellulose and hemi-cellulose in the biomass. The enzyme may be, for example, cellulase; hemi-cellulase; β 1-4 endoglucanases (E.C. 3.2.1.4), β 1-4 exoglucanases (E.C. 3.2.1.9.1), β-glucosidases (E.C. 3.2.1.2.1), endoxylanase, and combinations thereof. Combinations of these enzymes may be compositions of enzymes comprising cellulases, β-glucosidases and hemi-cellulase; or composition of enzymes comprising endoxylanase and cellulase. The addition of at least one enzyme, which includes a laccase enzyme described below, may occur after said treating step.

Further a laccase enzyme may be added to digest carbonyl scavenger which remains free in the depolymerized biomass or is attached to the biomass.

After the steam treatment and prior to the addition of the enzymes, the temperature of the biomass may be in excess of the enzyme inactivation temperature. Since a high temperature may inactivate enzymes by denaturing its amino acid chain, the enzyme may be added to the biomass at a point below the enzyme inactivation temperature. The enzymes may be added within the functional temperature(s) or optimal temperature(s) of the enzyme. To save energy, the enzymes may be added after the biomass has cooled below the inactivation temperature and that the enzymatic process is completed sufficiently before the temperature has dropped below the optimal functional temperature of the enzyme. Naturally, it is also an option to maintain a desired temperature by cooling or heating the biomass. Adding a dilution liquid, such as water at a certain temperature, may be used to cool the biomass.

Further, the enzyme may be added while the carbonyl scavenger is still active. The addition of laccase enzymes may act on the carbonyl scavenger.

In one embodiment, the enzyme pretreatment process may be performed at a specific temperature such as, for example at from 30° C. to 60° C.; 40° C. to 55° C.; or 45° C. to 50° C., or at room temperature or lower.

For any part of the process, the temperature can be maintained, increased or decreased, if desired, by heating or cooling, by mixing batches of different temperatures, or by the additional of solvents (e.g., water) which can be at a higher or lower temperature.

Enzymatic digestion may be performed, for example, within 24 hours after the addition of the carbonyl scavenger. The enzymatic digestion may be performed as soon as or soon after the biomass has cooled to the desired temperature.

The contacting of the biomass with an enzyme can be performed for a period of time up to one day. While longer enzymatic digestions are possible, a shorter period of time such as 60 minutes, 10 hours, 20 hours, 30 hours, 40 hours, 60 hours or 72 hours or any time less than these values or any time between any of two of these values may be used for practical or economic reasons. In another preferred embodiment, the enzymatic digestions can take 50, 100, 150 or 200 hours or any time less than these values or any time between any of two of these values. See, e.g., the examples section. In one embodiment, a preferred period of enzyme contact is about 3 days or less.

The processes of the disclosure produce fermentable sugar or sugars which may be a monomeric sugar. Examples of monomeric sugars include glucose, xylose, and a combination thereof.

One surprising benefit of the claimed process is that it is a significant improvement over the current processes in terms of efficiency. That is, the processes of this disclosure can convert 80% to 90%, 82% to 90%, 85% to 90%, at least 60%, at least 70%, at least 80%, at least 90% or at least 95% of the cellulose in a lignocellulosic material into a fermentable sugar. This is a higher level of efficiency than what is currently known.

Further aspects of the invention will be apparent to a person skilled in the art from the following description and claims, and generalizations thereto.

DETAILED DESCRIPTION

Figure 1:
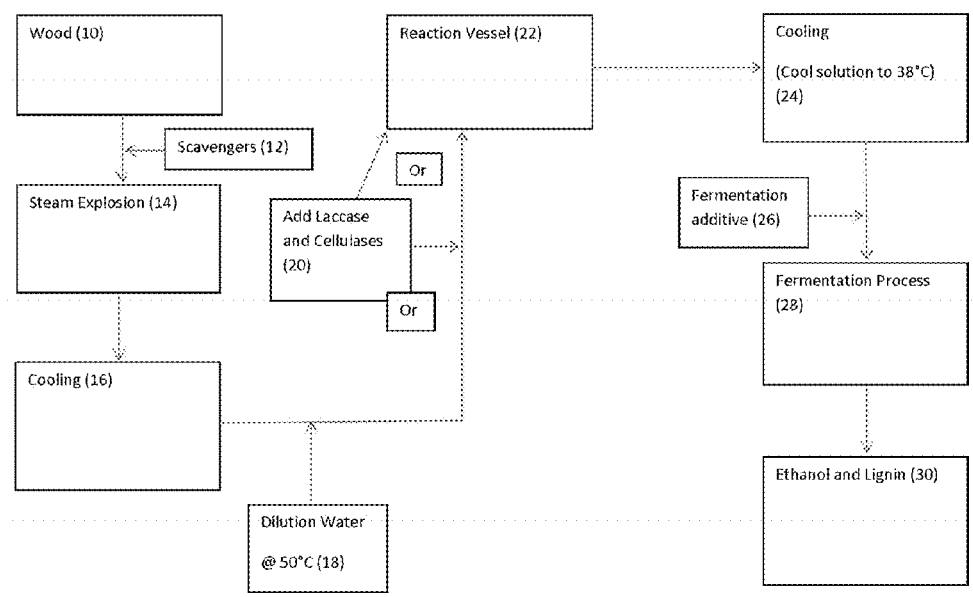
FIG. 1 is a flow chart showing an exemplary process to treat biomass to produce fermentable sugars.

As discussed in the background section, polymerized lignin protects a plant from pathogens and pests and provides rigidity. Unfortunately, the same qualities reduce the utility of lignocellulosic biomass by making it difficult to fully utilize the cellulose. Cellulose utility is not as high as desired because while lignin can be depolymerized during processing, it can also spontaneously repolymerize during processing. We have found a process for avoiding lignin's undesirable hindrance to full utilization of cellulose.

In the processing of biomass, steam treatment is often used as a first step in improving the accessibility of the starting product. During dilute acid steam treatment, including steam explosion treatment, of corn stovers as well as other forms of biomass (wood chips, etc.), depolymerization and repolymerization of lignin takes place. Often, repolymerization may occur at a slower speed than depolymerization leaving a significant fraction of the lignin in a depolymerized state at a point in time. When heated, lignin loses β-O-4' structures and form C—C condensed structures. As the treated material cools, repolymeriztion of the lignin occurs (condenses). Both the depolymerization and repolymerization reactions are thought to be mediated through a common intermediate, a carbonium ion, formed from the benzyl alcohol structures in the lignin.

Repolymerization of lignin is undesirable in the processing of biomass because depolymerized and repolymerization of the lignin results in lignin that is denser and which is less penetrable to cellulase than naturally occurring lignin. Our experimental evidence shows us that cellulase penetration is important to allow access of the enzymes to their substrate (cellulose) Since enzymes (e.g., cellulose) convert cellulose into sugars or individual fibers, it follows that a reduced diffusion of celluloses results in reduced efficiency in these production processes.

It is known that the addition of a carbonium scavenger compound, such as 2-naphthol, to the steam treatment phase is useful in the elimination of the repolymerization of lignin (see "Lignin depolymerization/repolymerization and its critical role for delignification of aspen wood by steam explosion", Jeibing Li, Gunnar Henriksson, Göran Gellerstedt, *Science Direct*, Dec. 1, 2006). However, the effects of a carbonium scavenger on enzymatic degradation of cellulose has not been studied or appreciated.

What is desired is a method to improve the enzymatic saccharification yield of biomass, including corn stovers, while inhibiting the repolymerization of lignin in a steam explosion process. In order to improve the enzymatic saccharification yield, we have studied the interaction of the carbonyl scavenger with enzymes.

Towards the goal of improving yield, a process has been developed to combine the use of the carbonium ion (carbonyl) scavenger (2-naphthol) or any other carbonyl scavenger with enzymatic treatment of biomass, in particular corn stovers, in a pretreatment phase to steam explosion. This combination produces surprisingly high yields of fermentable sugars which has not been achieved by conventional methods.

The addition of the carbonyl scavenger compound is useful in avoiding repolymerization of lignin, while the addition of enzymes such as cellulases and enzyme mixtures aids in the breaking of the cellulose and hemi-cellulose molecules into sugars useful in the production of ethanol. Examples of suitable enzymes include, at least, cellulase; hemi-cellulase; β 1-4 endoglucanases (E.C. 3.2.1.4), β 1-4 exoglucanases (E.C. 3.2.1.9.1), β-glucosidases (E.C. 3.2.1.2.1), endoxylanase, and combinations thereof.

As known from the Li article, repolymerization of the lignin can be prevented, or at least minimize to a sufficient degree, by the addition of a carbonyl scavenger compound such as 2-naphthol. It has been found, when pretreating biomass (corn stovers, wood chips, etc.) with the addition of enzymes, especially cellulase enzymes, an increase in the subsequent saccharification yield is experienced if the enzyme is added in the presence of the carbonyl scavenger. We note that Li relates to the production of lignin and Li does not appreciate the effects of the carbonyl scavenger on the availability of cellulose and hemicellulose to enzymatic degradation while these materials are still in mixture with lignin.

As shown above, we have found that cellulose and hemicellulose is surprisingly accessible to enzymatic degradation in the presence of a carbonyl scavenger and that physical separation of lignin and cellulose and hemi-cellulose is not required. Furthermore, we have surprisingly found that the carbonyl scavenger has no significant effect on the activity of the enzyme or the ability of the enzyme convert cellulose to fermentable sugars at a high yield even in the presence of lignin. This has not been achieved or attempted by the current state of technology.

The combination of carbonyl scavenger and enzyme has achieved the surprising result of improving saccharification yields from 75% to 80% for no carbonyl scavenger addition to 80% to 90% with carbonyl scavenger addition (i.e., the claimed method). That is, the amount of complex carbohydrate (as starch or cellulose) that is broken down into its monosaccharide components is increased from 75% to 80% to the improved rate of 80% to 90%. That is, the processes of this disclosure can improve the saccharification yields to 80% to 90%, 82% to 90% or 85% to 90%. Alternatively, the amount of enzymes used may be reduced. For example, to less than 3% such as 2.5%. In this case, the saccharification yield can improve more than 50%, more than 100% or more than 115%. See, Examples.

Not wishing to be bound by theory, we conclude that, in the disclosed process, the carbonyl scavenger compound prevents the repolymerization of the lignin, resulting in the better reactivity of the cellulose, thus keeping the lignin fibers open or un-reacted and thereby allowing the enzyme (cellulases, hemi-cellulases, or a combination thereof) to attach to the cellulose polymer and "bind" the cellulose polymer and then break up the molecules of cellulose into monomeric sugar components. These monomeric sugar components such as glucose, xylose, or a combination thereof are then useful as fermentable sugars.

Fermentable sugars released from biomass can be used by suitable microorganisms to produce a plurality of target chemicals. The fermentable sugars may be used, for example, as a component of a fermentation broth to make up between 10% to about 100% of the final fermentation medium.

Target chemicals that can be produced by fermentation include, for example, acids, alcohols, alkanes, alkenes, aromatics, aldehydes, ketones, biopolymers, proteins, peptides, amino acids, vitamins, antibiotics, and pharmaceuticals. Alcohols may include, at least, methanol, ethanol, propanol, isopropanol, butanol, ethylene glycol, propanediol, butanediol, glycerol, erythritol, xylitol, and sorbitol. Acids include acetic acid, lactic acid, propionic acid, 3-hydroxypropionic, butyric acid, gluconic acid, itaconic acid, citric acid, succinic acid and levulinic acid. Amino acids include glutamic acid, aspartic acid, methionine, lysine, glycine, arginine, threonine, phenylalanine and tyrosine. Additional target chemicals include methane, ethylene, acetone and industrial enzymes can also be produced.

The fermentation of sugars to target chemicals may be carried out by one or more appropriate biocatalysts in single or multistep fermentations using microorganisms such as wild type or recombinant bacteria, filamentous fungi and yeast. Such microorganisms include, at least, *Escherichia, Zymomonas, Saccharomyces, Candida, Pichia, Streptomyces, Bacillus, Lactobacillus*, and *Clostridium*. As a specific example, the fermentable sugars may be used, for example, for the production of ethanol using yeast, or *Z. mobilis* or for the production of 1,3-propanediol using *E. coli*.

FIG. 1 shows an exemplary process flow for a use of carbonyl scavengers and laccases and cellulases in a process to convert wood (lignocellulosic material) to ethanol and lignin. Wood or other lignocellulosic material 10 is treated with a carbonyl scavenger 12 compound such as 2-naphthol prior to steam explosion 14 of the wood or other lignocellulosic material. The wood or other lignocellulosic material with the carbonyl scavenger 12 are subjected to a steam explosion 14 treatment or other treatment that depolymerizes the lignin in the biomass. The product from steam explosion is allowed to cool 16 such as to about 50° C. It is understood that steam explosion may be replaced by another method of producing depolymerized lignin. Such a method may be, for example, dilute acid steam treatment. Once the cooled steam exploded material is cooled, dilution water 18, such as at temperature of about 50° C., is added to the steam exploded material.

The cooled steam exploded material, e.g., biomass with depolyimerized lignin, may include carbonyl scavengers 12 some of which are attached to the wood or other lignocellulosic material and others of which are not attached to the material. To address the residual carbonyl in the biomass, laccases or cellulase enzymes 20 or both may be added to the cooled steam exploded material. The term "or" means either or both. For example, the dilution water 18 may include laccases or cellulase enzymes which mix with the seam exploded material when the dilution water is added to the material. Alternatively and as shown in the FIG. 1, the laccases or cellulose enzymes may be added after the dilution water is added to the steam explosion product such as in a transport conduit between the dilution water coupling and a reaction vessel 22 or to the reaction vessel.

In the reaction vessel 22, the steam exploded material and enzymes of laccase and cellulase are retained for sufficient time to allow the enzymes to act upon the wood or other lignocellulosic material. Once the reaction is complete, the slurry is cooled 24 to a temperature which may be in a range or 35 to 40° C. After cooling, the fermentation additives 26 are added to the cooled steam exploded material such as downstream of the reaction vessel. The fermentation additives may include, but are not limited to, yeast. The cooled steam explosion material with the fermentation additives ferments 28 to produce ethanol and lignin 30. The ethanol and lignin may thereafter be separated and such that the ethanol and lignin are discharged separately from the process.

Enzymatic saccharification experiments performed on steam exploded and carbonyl scavenger treated lignocellulosic material have shown higher conversion of cellulose to glucose level as compared to conversions performed without the addition of these carbonyl scavengers additives. The action of these additives to the lignocellulosic material is thought to be related with the depolymerization and repolymerization reaction of lignin during the exposure to high temperature and pressures necessaries to improve its enzymatic digestion. It is known in the literature that carbonyl scavengers act as a lignin repolymerization blocker. It is postulated that if repolymerization is eliminated, the cellulosic portion of the material is more exposed to the action of enzymes.

Further fermentation of sugars obtained during enzymatic hydrolysis to form ethanol with *saccharomyces cereviciae* has shown that residual carbonyl scavengers are detrimental for growth. The carbonyl scavenger used in this study was 2-naphthol. The naphthols are naphthalene homologues of phenol, with the hydroxyl group being more reactive than in the phenols. The naphthols are considered highly nucleophilic and react with lignin to block the re-condensation of other close branches of phenolic compounds.

Alongside, laccases are copper-containing oxidase enzymes that are found in many plants, fungi, and microorganisms. Laccases act on phenols and similar molecules, performing one-electron oxidations, which remain poorly defined. It is proposed that laccases play a role in the formation of lignin by promoting the oxidative coupling of lignols, a family of naturally occurring phenols.

A hypothesis has been formulated that by the use of laccases after the reaction of carbonyl scavengers during pretreatment, the toxicity of these molecules is reduced or eliminated. The use of laccases added after steam explosion and in conjunction with the carbonyl scavengers added before steam explosion may be used to improve cellulosic saccharification and fermentations of pretreated lignocellulosic material.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

EXAMPLES

Example 1

Figure 2:
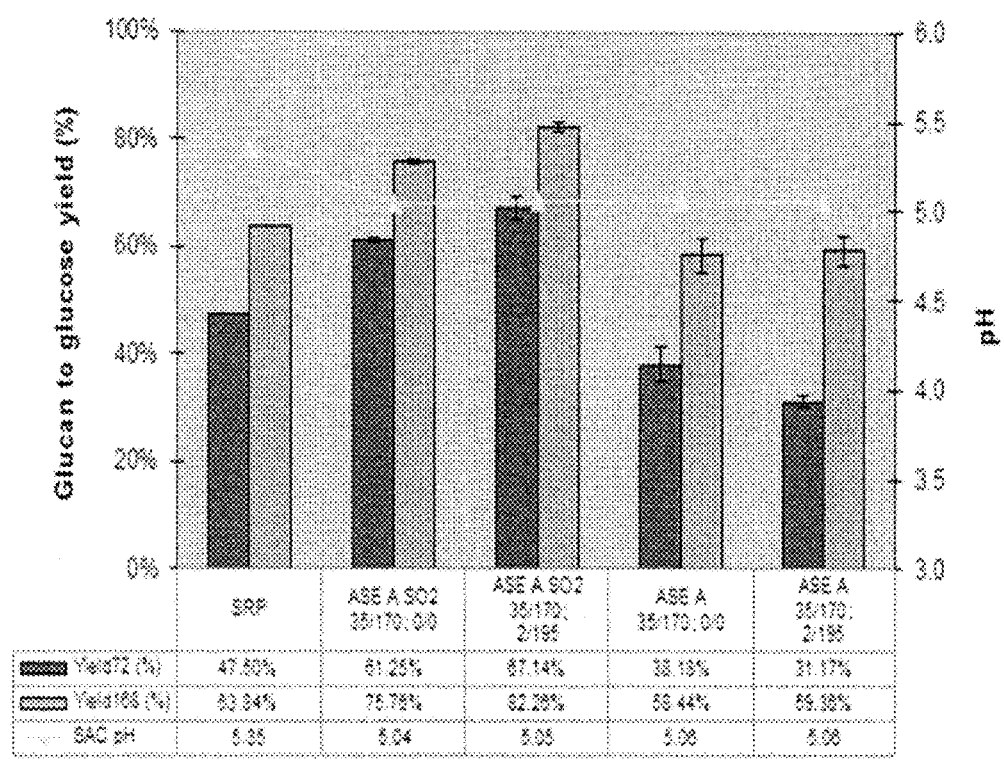
FIG. 2 depicts enzymatic saccharification yield (%) of non acid catalyzed pretreated corn stover impregnated with $SO_2$ and 2.5% enzyme dose.

Enzymatic Saccharification Yield (%) of Non Acid Catalyzed Pretreated Corn Stover Impregnated with $SO_2$ and 2.5% Enzyme Dose The experiments were performed as described above and the results are represented graphically in FIG. 2. In the figure, glucan to glucose yield (%) is a measurement of saccharification yield and should be considered the same as saccharification yield. SRP is standard reference pulp (Kraft pulp). ASE is advanced steam explosion. ASE is performed in two steps, a prehydrolysis step and a steam explosion step. In the figure caption, the first step (see, FIG. 2, "35/170") represents the first step of ASE which is prehydrolysis which is performed at 35 minutes at 170 degrees centigrade. The second step is steam explosion. There, "0/0" indicates that the second step is not performed while "2/195" indicates 2 minutes at 195 degrees centigrade. A refers to "autohydrolysis" and means that the experiment was peformed without the addition of additional acid. Yield72 and Yield168 refer to experiments performed with 72 hours and 168 hours of enzyme contact respectively. The SRP columns are positive control experiments mainly to ensure that the enzymes are active.

Example 2

Figure 3:
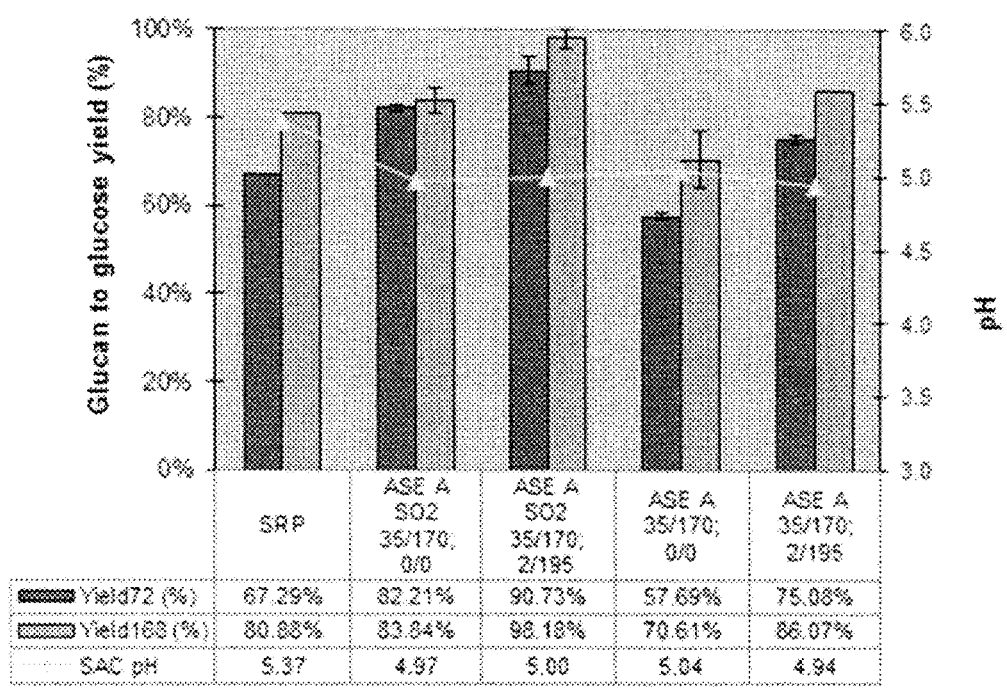
FIG. 3 depicts enzymatic saccharification yield (%) of non acid catalyzed pretreated corn stover impregnated with $SO_2$ and 6% enzyme dose.

Enzymatic Saccharification Yield (%) of Non Acid Catalyzed Pretreated Corn Stover Impregnated with $SO_2$ and 6% Enzyme Dose The experiments were performed as described above and the results are represented graphically in FIG. 3. Example 2 is performed under the same conditions as Example 1 with the exception that 6% of enzymes are used. The captions in FIG. 3 have the same meaning as the captions in FIG. 2.

As can be seen in both examples 1 and 2, the methods of this disclosure improve the yield of the reaction significantly. See, FIG. 2 where the improvements were at least 60% (61.25%/38.18%), 29% (75.75%/58.44%), 115% (67.14%/31.17%) and 38% (82.26%/59.36%). See, also, FIG. 3 where the improvements were at least 42% (82.21%/57.69%), 18% (83.84%/70.61%), 20% (90.73%/75.08%) and 14% (98.18%/86.07%).

I claim:

1. A method for treating a biomass comprising a lignocellulosic material to produce fermentable sugars through saccharification comprising:
   treating the biomass to produce a biomass with a depolymerized lignin;
   adding a carbonium-ion scavenger to the biomass before, during, or after said treating step to inhibit repolymerization of the lignin;
   adding a laccase enzyme and a cellulase enzyme to the biomass with depolymerized lignin subsequently to the addition of the carbonium-ion scavenger; and
   producing a fermentable sugar from the enzymatic actions of the laccase enzyme and cellulase enzyme in the presence of the carbonium-ion scavenger on the biomass with depolymerized lignin;
   wherein the carbonium-ion scavenger is 2-naphthol.

2. The method of claim 1 wherein the treating step is a dilute acid steam treatment or a steam explosion treatment.

3. The method of claim 1 wherein said treating step is performed while said cabonium-ion scavenger is still active in inhibiting repolymerization of said lignin.

4. The method of claim 1 wherein said cellulase enzyme is selected from the group consisting of cellulase, hemi-cellulase, β 1-4 endoglucanases (E.C. 3.2.1.4), β 1-4 exoglucanases (E.C. 3.2.1.91), endoxylanases and combinations thereof.

5. The method of claim 1 wherein the laccase enzyme and cellulase enzyme are added to said biomass when said biomass is at a temperature below the enzyme inactivation temperature.

6. The method of claim 1 wherein the laccase enzyme and cellulase enzyme are added to said biomass when said biomass is at a temperature from 30° C. to 60° C.

7. The method of claim 1 wherein the laccase enzyme and cellulase enzyme are added within 24 hours after the addition of carbonium-ion scavenger.

8. The method of claim 1 wherein the fermentable sugar comprises glucose, xylose, or a combination thereof.

9. The method of claim 1 wherein said method converts 60-90% of the cellulose in a biomass into a fermentable sugar.

10. The method of claim 1 wherein said method is performed without the addition of acids.

* * * * *